United States Patent
Vögelin et al.

(10) Patent No.: US 8,100,854 B2
(45) Date of Patent: Jan. 24, 2012

(54) VALVE, IN PARTICULAR FOR A BREAST SHIELD SET

(75) Inventors: Stefan Vögelin, Auw (CH); Urs Stadelmann, Pfeffikon (CH)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 10/588,463

(22) PCT Filed: Feb. 6, 2006

(86) PCT No.: PCT/CH2006/000070
§ 371 (c)(1),
(2), (4) Date: Aug. 23, 2006

(87) PCT Pub. No.: WO2006/105675
PCT Pub. Date: Oct. 12, 2006

(65) Prior Publication Data
US 2007/0179439 A1    Aug. 2, 2007

(30) Foreign Application Priority Data
Apr. 7, 2005 (CH) .......................... 638/05

(51) Int. Cl.
*A61M 1/06* (2006.01)
(52) U.S. Cl. ........................................ 604/74
(58) Field of Classification Search .......... 604/30, 604/32, 33, 73–76, 167.01–167.03, 236, 604/237, 241, 246–249, 256, 322–326, 346, 604/533, 537, 905; 137/512.15, 599.01, 137/843, 852, 859
See application file for complete search history.

(56) References Cited

U.S. PATENT DOCUMENTS

| | | | | |
|---|---|---|---|---|
| 3,827,456 A | * | 8/1974 | Sheppard | 137/859 |
| 3,981,636 A | * | 9/1976 | Aoki et al. | 417/566 |
| 4,181,477 A | * | 1/1980 | Litt | 417/560 |
| 4,680,028 A | * | 7/1987 | Stuart | 604/74 |
| 4,799,922 A | * | 1/1989 | Beer et al. | 604/74 |
| 4,813,932 A | * | 3/1989 | Hobbs | 604/74 |
| 5,025,829 A | | 6/1991 | Edwards et al. | |
| 5,358,476 A | * | 10/1994 | Wilson | 604/74 |
| 5,360,413 A | * | 11/1994 | Leason et al. | 604/249 |
| 5,415,632 A | * | 5/1995 | Samson | 604/74 |
| 5,453,097 A | * | 9/1995 | Paradis | 604/247 |
| 5,897,033 A | * | 4/1999 | Okawa et al. | 222/212 |
| 6,042,560 A | * | 3/2000 | Niederberger | 604/74 |
| 6,110,141 A | * | 8/2000 | Nuesch | 604/74 |

(Continued)

FOREIGN PATENT DOCUMENTS
DE   197 47 842 A1   5/1999
(Continued)

*Primary Examiner* — Kevin C Sirmons
*Assistant Examiner* — Kami A Bosworth
(74) *Attorney, Agent, or Firm* — McDonnell Boehnen Hulbert & Berghoff LLP

(57) ABSTRACT

The valve includes a valve seat and a valve body with a circular diaphragm. The valve body is arranged over the valve seat in order to close the latter sealingly when it bears on the valve seat. The valve seat and the valve body have openings which are offset relative to one another and which form a free passage when the diaphragm of the valve body lifts. The diaphragm of the valve body has elongate openings which are uniformly distributed along a circle in the periphery of the diaphragm, the circle having approximately the same center point as the diaphragm. The elongate openings are separated from one another by webs, the diaphragm being designed to be weaker in the area adjacent to these webs.

16 Claims, 8 Drawing Sheets

U.S. PATENT DOCUMENTS

| | | | |
|---|---|---|---|
| 6,270,474 B1 * | 8/2001 | Nuesch | 604/74 |
| 6,289,521 B1 * | 9/2001 | Ikeda | 2/421 |
| 6,390,130 B1 * | 5/2002 | Guala | 137/859 |
| 6,508,792 B2 * | 1/2003 | Szames et al. | 604/237 |
| 6,764,286 B2 * | 7/2004 | Hunnicutt et al. | 417/470 |
| 2003/0153869 A1 * | 8/2003 | Ytteborg | 604/74 |
| 2004/0015127 A1 * | 1/2004 | Silver et al. | 604/74 |
| 2004/0250864 A1 * | 12/2004 | Zelson | 137/859 |
| 2007/0173756 A1 | 7/2007 | Krebs et al. | |

FOREIGN PATENT DOCUMENTS

| | | |
|---|---|---|
| EP | 1 099 455 A2 | 5/2001 |
| WO | WO 03/092 768 A2 | 11/2003 |
| WO | WO 2005/118023 A1 | 12/2005 |

* cited by examiner

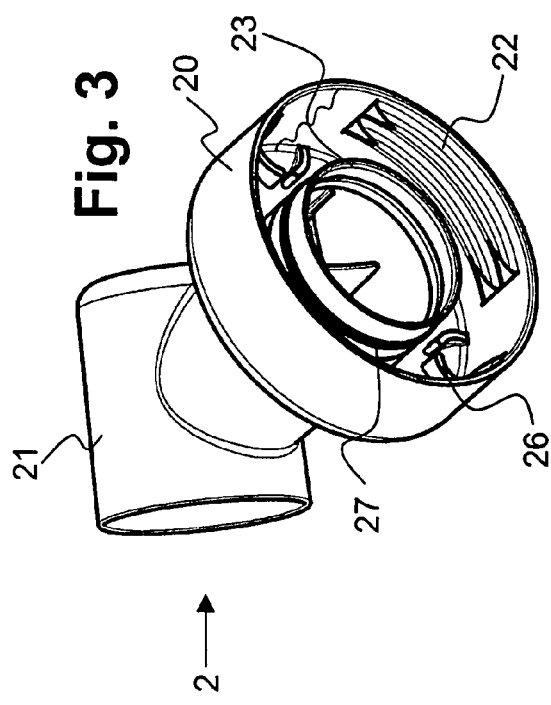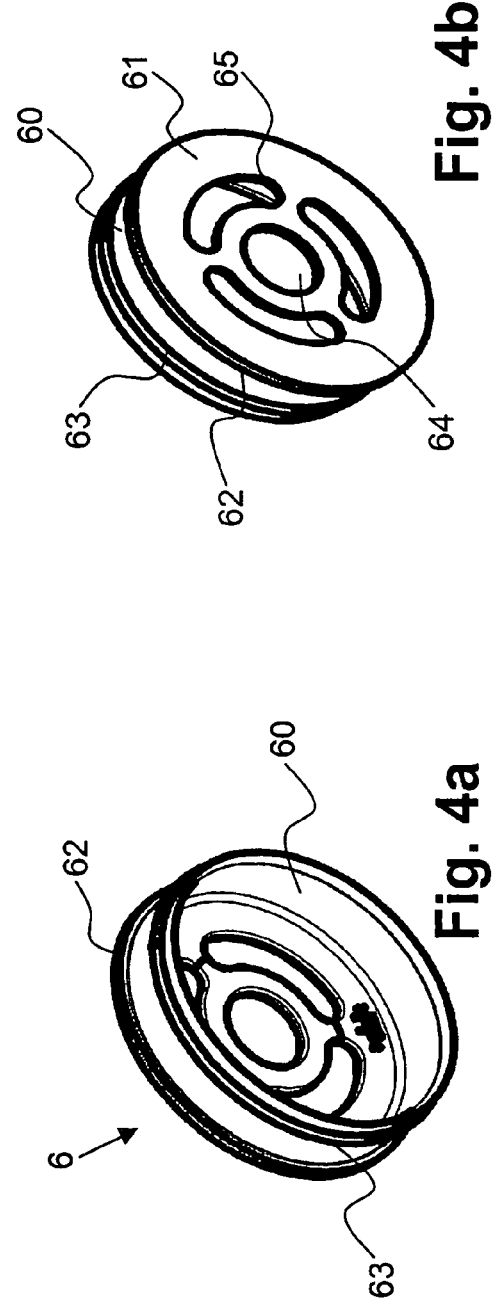

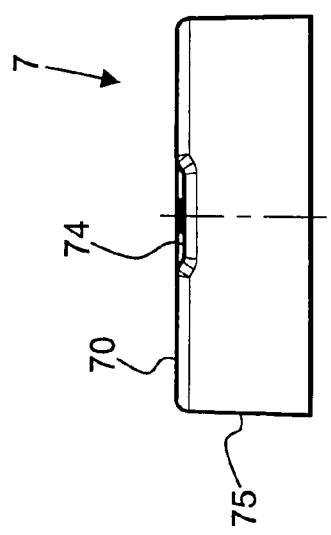
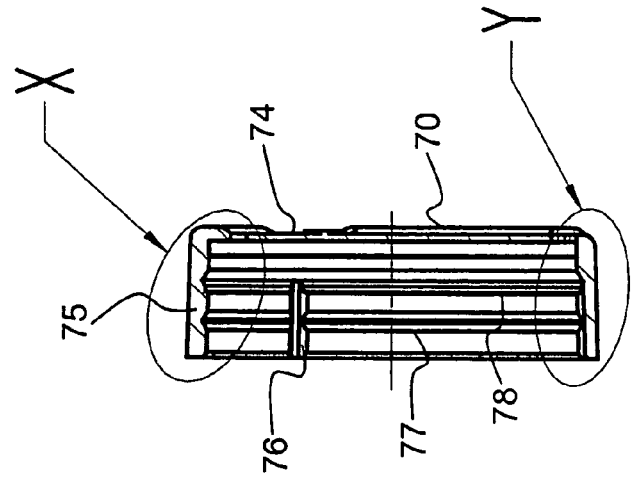
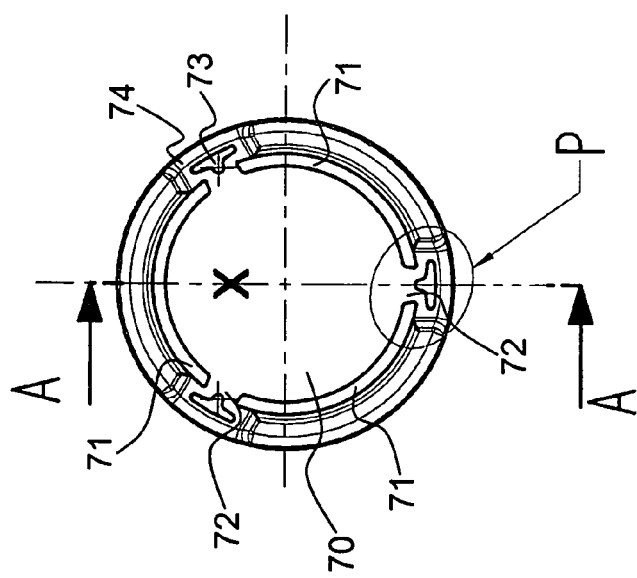

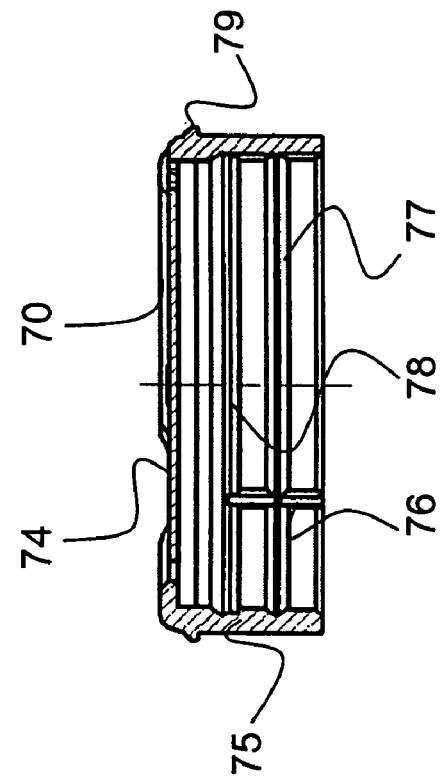
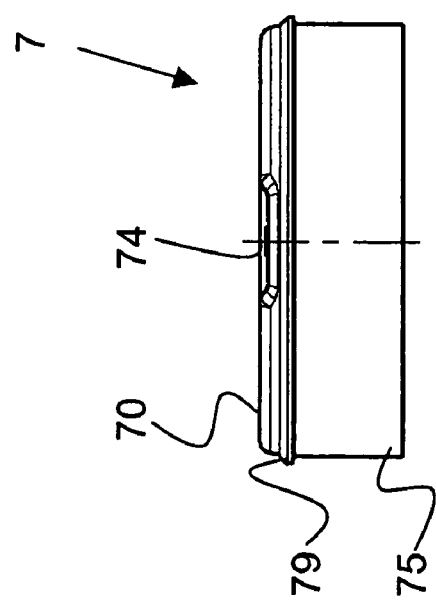

US 8,100,854 B2

VALVE, IN PARTICULAR FOR A BREAST SHIELD SET

FIELD OF THE INVENTION

This application is a 371 application of PCT/CH06/00070 filed Feb. 6, 2006 which claims priority to Swiss application number 638/05 filed Apr. 7, 2005, the contents of which are fully incorporated herein.

The invention relates to a valve as claimed. The valve is suitable in particular for use in a breast shield set. The invention further relates to a breast shield set for pumping off human breast milk as claimed.

BACKGROUND

Breast shield sets are used together with breast pumps for pumping off human breast milk. They usually comprise a breast shield with a breast shield funnel for placing on the human mother's breast, a first connector part for connection to a milk collection vessel, and a second connector part for attachment to a mechanical or electrical pump or for attachment to a suction line of such a pump.

To pump off the breast milk, the breast shield funnel is placed as tightly as possible on the mother's breast, and a vacuum is generated cyclically in the breast shield funnel by means of the pump. To keep the space to be evacuated as small as possible, i.e. to minimize the dead volume, the breast shield set has a nonreturn valve in the direction of the milk collection vessel. This nonreturn valve is opened toward the interior of the milk collection vessel by means of the pressure of the aspirated milk and, when a vacuum is applied, closes said vessel off relative to the evacuated volume of the rest of the breast shield set.

The valve has a valve seat which is covered by a valve body in the form of a diaphragm flap secured at one end. When the milk flowing in is at sufficient pressure, the diaphragm flap is opened toward the interior of the vessel. This valve has indeed proven effective in practice. However, such breast shield sets are relatively expensive to manufacture. Since the market increasingly requires that these breast shield sets should, for hygiene reasons, be used just once or at most only a few times, there is a need to reduce the manufacturing costs as much as possible.

Since these breast shield sets are therefore to be used only a few times at most, the individual parts should be able to be produced as inexpensively as possible. This applies also in particular to the nonreturn valve. Since, however, the breast shield set should be cleaned after each use, the valve must also be constructed as simply as possible and be correspondingly easy to clean. Moreover, it must not distort during cleaning, in order to subsequently ensure sufficient sealing. The shape, configuration and choice of material of the valve play an important role in achieving these objects. The breast shield sets are usually made from plastic, in particular polyethylene (PE), polypropylene (PP) or polycarbonate (PC), while the valve body itself is made of silicone.

SUMMARY OF THE INVENTION

It is therefore an object of the invention to make available a valve which can be produced inexpensively and which nevertheless permits a secure seal.

This object is achieved by a valve having the features as claimed.

The valve according to the invention comprises a valve seat and a valve body with a circular diaphragm. The valve body is arranged over the valve seat in order to close the latter sealingly when it bears on the valve seat. The valve seat and the valve body have openings which are offset relative to one another and which form a free passage when the diaphragm of the valve body lifts. The diaphragm of the valve body has elongate openings which are uniformly distributed along a circle in the periphery of the diaphragm, the circle preferably having approximately the same center point as the diaphragm. The elongate openings are arc-shaped, their longitudinal dimension extending along said circle. They are separated from one another by webs or bridges. In other words, the elongate openings form a common circular ring whose width is a multiple smaller than the smaller radius of the circular ring and which is provided with webs. The diaphragm is designed to be weaker in the area adjacent to these webs or bridges.

There are preferably exactly three such openings and exactly three webs, with the result that the diaphragm is held in a peripheral three-point suspension.

The weakened areas can be compact openings or thinned parts or preferably a combination of these. These weakened areas help to compensate stresses, such that the functionality of the valve is guaranteed even after it has been cleaned by heating.

Good results have been achieved with T-shaped compact openings.

The combination of thinned areas and compact openings has the advantage that the webs forming the valve articulation are sufficiently flexible, even after cleaning, to ensure that the diaphragm circle formed by the elongate openings is able to lift and fall sufficiently quickly.

A cylindrical jacket is preferably formed integrally on the diaphragm and is pushed over a collar of the valve seat. If the jacket has axially extending notches and/or circumferential grooves on its inside face, distortion during cleaning is likewise avoided.

The described valve according to the invention, in the aforementioned embodiments and also in embodiments described below, is preferably used in breast shield sets of the type mentioned in the introduction. However, it can also be used in other articles, in particular in medical products, for example for drainage bags for aspiration of body fluids or in suction lines of any kind.

It is therefore a further object of the invention to make available a breast shield set that can be produced as inexpensively as possible.

This object is achieved by a breast shield set having the features as claimed.

To satisfy the hygiene regulations for repeat use, breast shield sets are usually able to be sterilized and autoclaved. However, increased demands placed on hygiene, both in hospital use and in private use, have in recent times prompted a need for breast shield sets that permit only a limited degree of repeat use. This repeat use is normally limited to a single day.

It is therefore a further object of the invention to make available a breast shield set that allows only a limited degree of repeat use.

This object is achieved by a breast shield set having the features as claimed.

The breast shield set according to the invention has at least one part that is not able to be autoclaved. It suffices entirely if this is the valve body. If the valve body is autoclaved, it distorts, and the functionality of the whole breast shield set is no longer guaranteed, because of lack of leaktightness and a consequent increase in dead volume.

It is also possible for several parts to be made from non-autoclavable material, for example the valve seat, the breast shield connector and the breast shield funnel. Of course, other accessories such as the suction line can be made from a non-autoclavable material.

The solution according to the invention results from the following observation:

Neonatal or maternity wards of hospitals are themselves normally able to clean the breast shield sets, so that the mothers can in each case reuse their own respective breast shield set. Moreover, the mothers or nursing staff are able to check how often the breast shield set has already been used, and it can be disposed of after a suitably short time. Autoclavable breast shield sets are normally cleaned in another department, so that they have to leave the neonatal or maternity wards and often arrive back in the ward only the next day, and the aforementioned possibilities of verification are therefore no longer afforded. If it is now possible to prevent the breast shield sets from being autoclaved, the desired limited degree of repeat use is possible.

However, the requirement that the valve body should no longer be able to be autoclaved means that the choice of material is greatly restricted. A thermoplastic elastomer (TPE) is suitable as the material. However, this material places considerable demands on the form of the valve body to ensure that it cannot distort during cleaning. The valves as claimed meet these demands.

Further advantageous embodiments are set forth in the dependent patent claims.

BRIEF DESCRIPTION OF DRAWINGS

The subject of the invention is explained in more detail below on the basis of preferred illustrative embodiments depicted in the attached drawing, in which:

FIG. 3 shows a perspective view of a breast shield connector;

FIG. 4a shows a perspective view of a valve seat;

FIG. 4b shows a further perspective view of the valve seat according to FIG. 4a;

FIG. 4c shows a side view of the valve seat according to FIG. 4a;

FIG. 4e shows an enlarged cross section through part of the valve seat according to FIG. 4a;

FIG. 5a shows a side view of a valve body;

FIG. 5b shows a view of the valve body according to FIG. 5a from above;

FIG. 5c shows a cross section through the valve body along A-A according to FIG. 5b;

FIG. 5e shows a perspective view of the valve body according to FIG. 5a;

FIG. 5f shows a further perspective view of the valve body according to FIG. 5a;

FIG. 6a shows a side view of a valve body according to a second embodiment;

FIG. 6b shows a cross section through the valve body according to FIG. 6a, and

DETAILED DESCRIPTION OF THE EMBODIMENTS OF THE INVENTION

Figure 1:
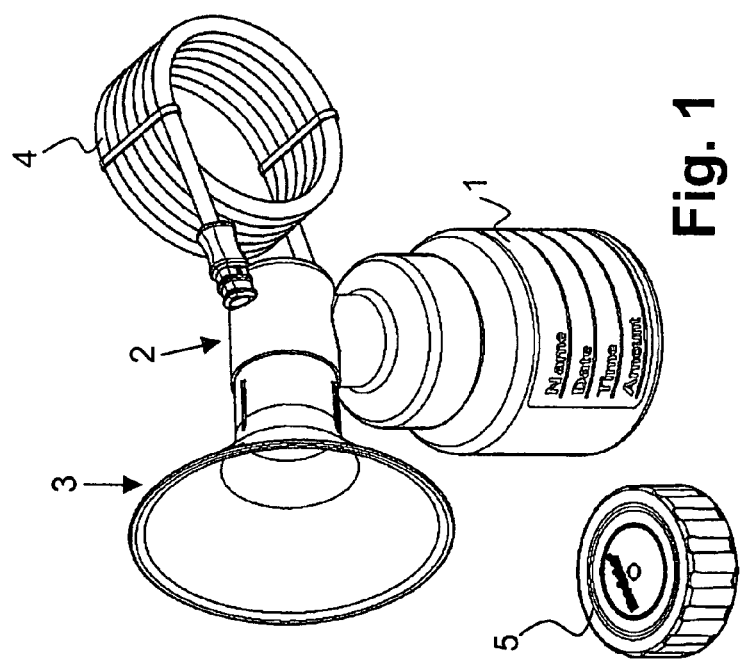
FIG. 1 shows a perspective view of the breast shield set including the collection vessel, suction line and closure lid.

FIG. 1 shows a breast shield set according to the invention. A breast shield connector 2 is screwed onto a milk collection vessel 1. A breast shield 3 with a breast shield funnel 30 is secured on one end of the breast shield connector 2, and a suction line 4 is secured at the other end. Instead of the breast shield connector 2, a closure lid 5 can be screwed onto the milk collection vessel 1, for example when the collection vessel 1 is filled.

Figure 2:
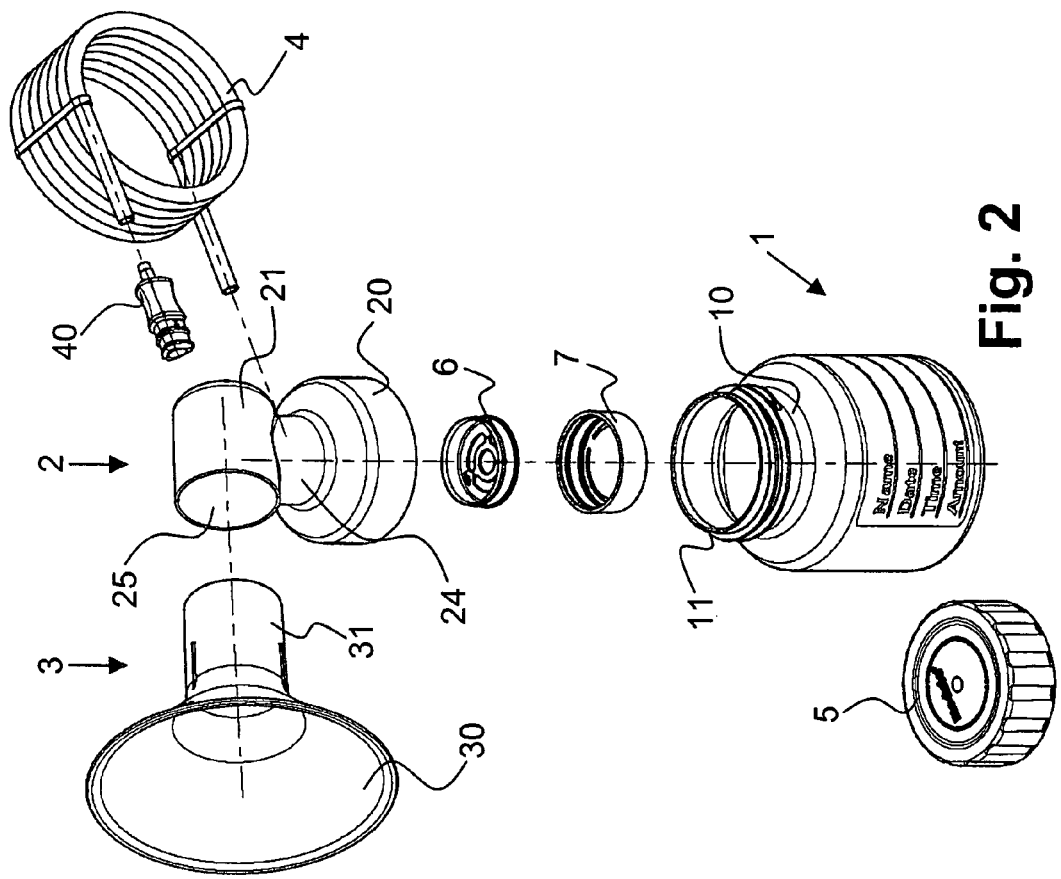
FIG. 2 shows an exploded view of the breast shield set according to FIG. 1.

FIG. 2 shows how the individual aforementioned parts can be connected to one another. The collection vessel 1 has a neck 10 with an outer thread 11 onto which a threaded attachment 20 with an inner thread 22 (FIG. 3) of the breast shield connector 2 can be screwed. A connector piece 21 is formed integrally on this threaded attachment 20 via a short neck 24. The connector piece 21 has a receiver opening 25 into which a coupler 31 of the breast shield 3 can be fitted. At the opposite end of the connector piece 21, a socket (not shown) is provided for direct attachment to the suction line 4. With the coupling piece 40, the tube 4 can be connected to an external breast pump.

The breast shield 3 can also be formed integrally on the breast shield connector 2. Moreover, the breast shield connector 2 can have, instead of the suction line socket, a receiver for a manual or electric motor.

As is also shown in FIG. 2, a valve with a valve seat 6 and with a valve body 7 secured on the latter is present between the breast shield connector 2 and the collection vessel 1. This valve is preferably arranged in the breast shield connector 2. The valve seat 6 can be formed integrally on the breast shield connector 2 or can be fitted onto a corresponding receiver 23. This corresponding valve receiver 23 in the form of an inwardly protruding neck can be seen in FIG. 3. Reference number 26 designates upper abutments for the milk collection vessel or breast milk bottle.

The valve seat 6 is shown in FIGS. 4a to 4e. It has a circular cover surface 61 which is substantially plane or absolutely plane and, formed integrally thereon, a peripheral collar 60. In the cover surface 61, there is a central opening 64 and peripheral openings 65. The peripheral openings 65 preferably form a common circle whose center point coincides with the center point of the circular cover surface 61. Exactly three peripheral openings 65 are preferably present, the common circle being interrupted by webs 66. As can best be seen from FIGS. 4c and 4e, the cover surface 61 protrudes from the collar 60 with a circumferential edge 62. Moreover, the collar 60 has a circumferential bead 63 in the lower area remote from the cover surface 61. This part can also be inscribed. A suitable example is designated by reference number 67 in the figures.

The valve body 7 is shown in FIGS. 5a to 5k. This valve body 7 can be fitted over the above-described valve seat 6. The valve is held in the breast shield connector 2 with the bead 27 and preferably with the first groove 77 or the second groove 78.

The valve body 7 has essentially the same basic shape as the valve seat 6, i.e. it has a circular, substantially plane diaphragm 70 which is surrounded by a peripheral cylindrical jacket 75. The diaphragm 70, however, can also have knobs on its outside face directed away from the valve seat 6. The diaphragm 70 has areas 74 which are designed to be weaker. This weakening is obtained, on the one hand, by the fact that these areas 74 have a smaller material thickness, as can be seen from FIG. 5a. On the other hand, compact openings 73 are present. The thinner areas or recesses 74 preferably have a constantly increasing transition to the rest of the diaphragm. FIG. 5a shows that the edge areas of these areas 74 are designed as ramps. This can also be seen from FIG. 5e.

As is shown in particular in FIG. 5b, the diaphragm 70, except for a small number of openings 71, 73, is designed substantially as a closed surface connected to its jacket 75 and secured in a three-point suspension. In particular, openings 71, 73 are present only in the peripheral area, not in the central area.

The diaphragm 70 shown has two types of openings 71, 73: narrow, elongate openings 71, and small, compact openings 73.

The elongate openings 71 are arranged in the peripheral area along the circumference of the diaphragm 70. In the example shown, three openings 71 of equal length and of equal size are present, each opening 71 extending by an angle of less than 120°. However, another number of openings can also be present. The openings 71 are, however, preferably arranged in a rotationally symmetrical manner in the peripheral area of the diaphragm.

They form a common circle whose center point preferably coincides with the center point of the diaphragm 70 or cover surface. This circle is interrupted by webs 72 or bridges. The smaller openings 73 are arranged in the area adjacent to these webs 72 and to the peripheral openings 71. One small compact opening 73 is preferably situated between each elongate opening 71. In this example, therefore, there are also three of these compact openings 73. These openings 73 preferably have a T-shaped configuration, with a foot and with a bar extending transversely over the latter. The foot is oriented radially toward the webs and to the center point of the diaphragm 70, and the bar is directed outward toward the periphery. The foot preferably ends on the outside of the circle formed by the peripheral openings 71. The bars of the individual openings 73 preferably lie on a circle whose center point coincides with the center point of the diaphragm. The bars are preferably curved in accordance with this circle, as can be seen in FIG. 5g.

The T-shaped openings 73 are located entirely within the weakened areas or recesses 74. However, the recesses 74 are slightly wider than the openings 73 themselves, at least in the area of the bars of said openings 73.

Figure 5F:
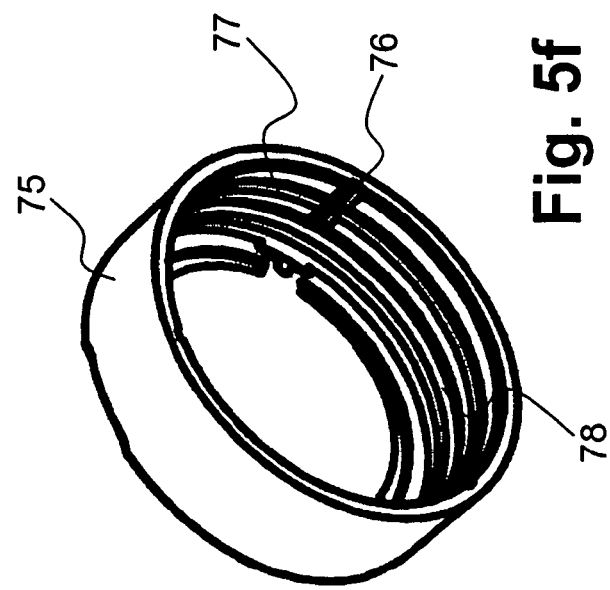
Figure 5D:
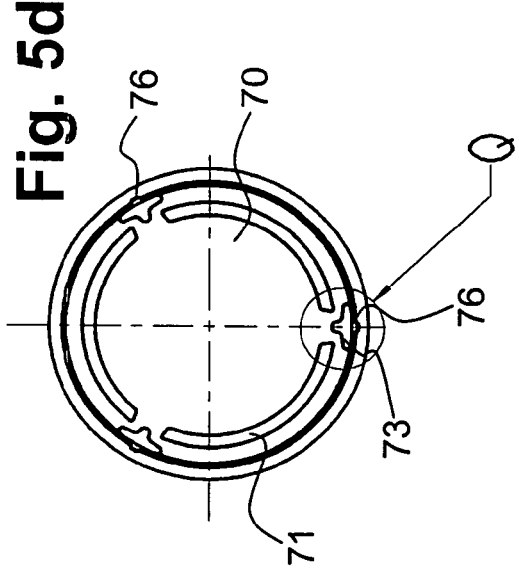
FIG. 5d shows a view of the valve body according to FIG. 5a from below.
Figure 5E:
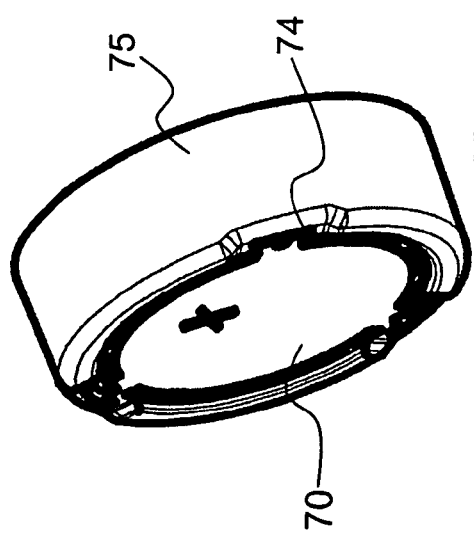
Figure 5H:
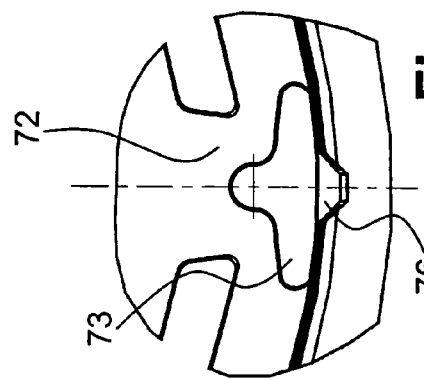
FIG. 5h shows an enlarged detail Q according to FIG. 5d.
Figure 5K:
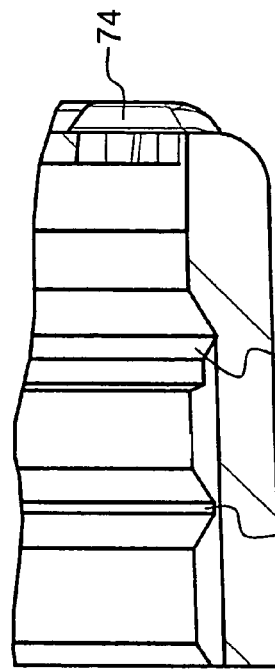
FIG. 5k shows an enlarged detail Y according to FIG. 5c.
Figure 5G:
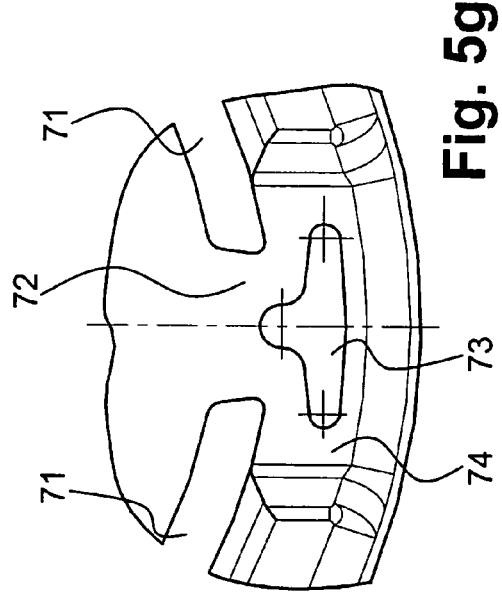
FIG. 5g shows an enlarged detail P according to FIG. 5b.
Figure 5I:
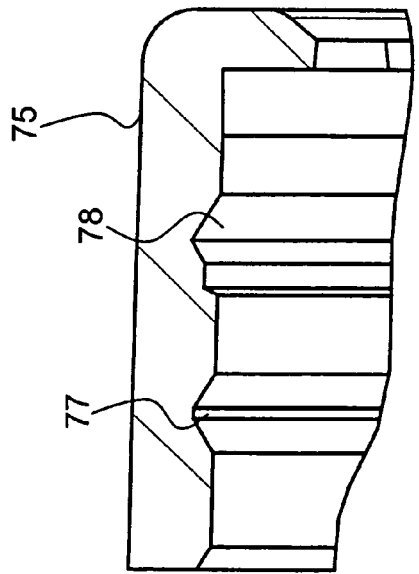
FIG. 5i shows an enlarged detail X according to FIG. 5c.

According to FIGS. 5c, 5i and 5k, the jacket 75 of the valve body 7 is preferably plane on its outside. The inner face of the valve body 7, however, has at least one, preferably two circumferential grooves 77, 78. Moreover, at least one notch 76 extending transversely relative to the circumferential grooves 77, 78 and therefore parallel to a center axis of the cylinder is provided, as is shown in FIG. 5f. This notch 76 preferably starts at the groove 78 lying nearer the diaphragm and ends on the outer edge of the jacket 75. In the present example, three notches 76 are provided which are each located in the area of the T-shaped openings 73, preferably in the line defined by the foot. This can be seen from FIGS. 5d and 5h. The grooves 77, 78 and notches 76 help avoid distortion of the jacket in the event of temperature changes, in particular during sterilization.

Figure 4E:
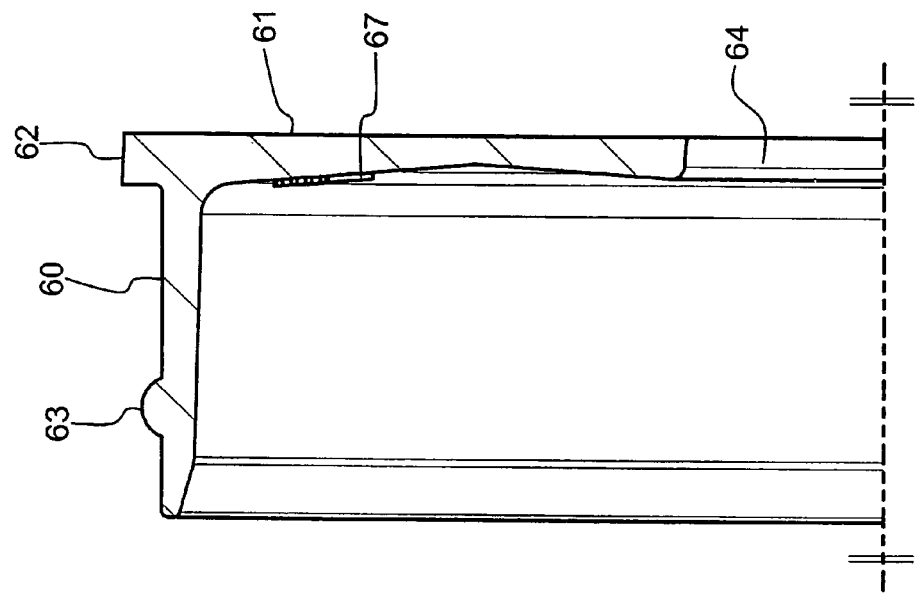
Figure 4C:
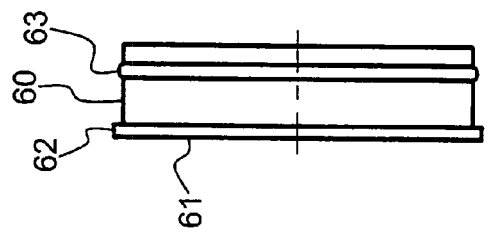
Figure 4D:
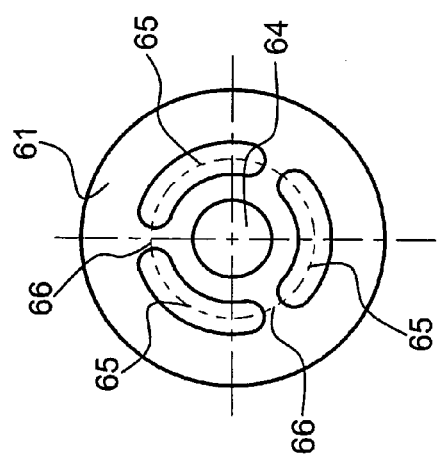
FIG. 4d shows a view of the valve seat according to FIG. 4a from above.

When the valve body 7 is arranged on the valve seat 6, as can be seen from comparison of FIGS. 4d and 5b, the central opening 64 and the peripheral openings 65 of the valve seat 6 are covered by the circular diaphragm flap which is located inside the elongate openings 71. The elongate openings 71 and the compact openings 73, by contrast, lie on the outer edge area of the valve seat 6. In this way, the valve is closed at normal pressure. If the pressure on the diaphragm flap is now increased, it curves uniformly toward the interior of the collection vessel 1 and frees the openings 64, 65 of the valve seat.

By this means, the openings 71, 73 of the valve body 7 also move away from their bearing surface, and passages are formed leading from one side of the valve to the other. When the pressure on the inside of the diaphragm subsides, the latter drops back onto the valve seat and closes the nonreturn valve.

The above-described individual parts of the breast shield set are preferably made from a sterilizable and autoclavable material, for example polypropylene (PP). However, at least one part, preferably the valve body, is made from a non-autoclavable material, for example a thermoplastic elastomer (TPE). It is preferable for only the valve body to be made from such a material.

Although the valve according to the invention has been described with reference to its use in a breast shield set, it can also be employed in other areas, for example in drainage bags or drainage containers for aspiration of body fluids, in vacuum hoses or in other medical or nonmedical devices.

Figure 6C:
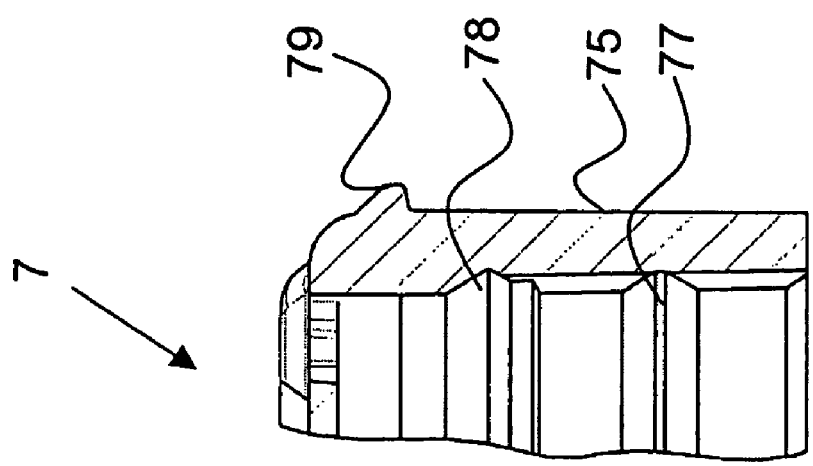
FIG. 6c shows an enlarged detail according to FIG. 6b.

FIGS. 6a to 6c show a second preferred embodiment of the valve body 7. It can be used together with the valve seat 6 described above. Except for an external bead 79, it has the same design as the above-described first illustrative embodiment of the valve body 7. This external bead 79 preferably extends about the entire circumference of the jacket 75. However, it can also be interrupted in places. It is also preferably arranged in the edge area of the jacket 75 adjacent to the diaphragm 70. By virtue of this bead 79, the valve body 7 can be more easily released from the valve seat 6 by hand, because the bead 79 improves the grip of the surface. A groove can also be used instead of or in addition to the bead 79. The jacket surface can likewise be provided with knobs, recesses or axially extending ribs.

The valve according to the invention is simple and inexpensive to manufacture, is reliable in its use, and scarcely deforms at all even in the case of considerable variations in temperature.

The invention claimed is:

1. A breast shield set for pumping off human breast milk, the breast shield set comprising a breast shield, a breast shield connector with a threaded attachment for connection to a milk collection vessel, and a valve for limiting a dead volume during pumping off of breast milk, wherein the valve has a valve seat and a valve body with a circular diaphragm, the valve body being arranged over the valve seat and closing the valve seat sealingly when it bears on said valve seat, and the valve seat and valve body having openings which are offset relative to one another and which form a free passage when the diaphragm of the valve body lifts, wherein said openings of the diaphragm of the valve body comprise narrow elongate openings with a long dimension and which are uniformly distributed adjacent the periphery of the diaphragm, and wherein the narrow elongate openings are separated from one another by webs, the diaphragm being designed to be weaker in the area adjacent to these webs and wherein said openings of the diaphragm further comprise compact openings which are present in areas generally between said narrow elongate openings, with said compact openings being smaller than said narrow elongate openings and having a T-shaped configuration comprising a foot and a bar extending transversely over the foot, the bar extending adjacent said periphery and the foot being oriented toward the webs and radially toward a center point of the circle of the diaphragm.

2. The breast shield set as claimed in claim 1, in which the valve seat of the valve can be fitted onto the breast shield connector or is formed integrally on the breast shield connector.

3. The breast shield as claimed in claim 1, in which the breast shield connector, the breast shield and the valve seat are made from an autoclavable material and the valve body is made from a non-autoclavable material.

4. The breast shield set as claimed in claim 3, in which the autoclavable material is polypropylene (PP) and the non-autoclavable material is a thermoplastic elastomer (TPE).

5. The breast shield as claimed in claim 1, in which the narrow elongate openings form a common circular ring whose width is a multiple smaller than the smaller radius of the circular ring and which is provided with webs.

6. The breast shield as claimed in claim 1, in which exactly three narrow elongate openings and exactly three webs are present.

7. The breast shield as claimed in claim 1, in which the compact openings are arranged in the weakened area of the diaphragm.

8. The breast shield as claimed in claim 1, in which the valve body has a cylindrical jacket that surrounds the diaphragm.

9. The breast shield as claimed in claim 8, wherein the diaphragm, except for the narrow elongate openings and compact openings and weakened areas, is designed as a plane, closed disk, which is connected circumferentially to the cylindrical jacket.

10. The breast shield as claimed in claim 8, in which the jacket has at least one notch extending parallel to a center axis of the cylindrical jacket.

11. The breast shield as claimed in claim 8, in which the cylindrical jacket has an inner face provided with at least one groove extending at least partially about the circumference.

12. The breast shield as claimed in claim 8, in which the cylindrical jacket is provided with a bead extending at least partially about the circumference.

13. The beast shield as claimed in claim 1, in which the valve seat has a plane surface with a central opening and with openings extending around this central opening, the extending openings being interrupted by webs.

14. The breast shield as claimed in claim 1, in which at least one part of the valve is made from a non-autoclavable material.

15. The breast shield as claimed in claim 14, in which the valve body is made from a non-autoclavable material.

16. The breast shield as claimed in claim 15, in which the valve body is made from a thermoplastic elastomer (TPE).

* * * * *